US00PP14803P2

(12) United States Plant Patent
Zary

(10) Patent No.: US PP14,803 P2
(45) Date of Patent: May 18, 2004

(54) FLORIBUNDA ROSE PLANT NAMED 'JACTOSAM'

(50) Latin Name: *Rose hybrida*
Varietal Denomination: JACtosam

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 10/300,577

(22) Filed: Nov. 19, 2002

(51) Int. Cl.[7] ..... A01H 5/00
(52) U.S. Cl. ..... Plt./149
(58) Field of Search ..... Plt./149, 147, 141, Plt./146, 136, 138

*Primary Examiner*—Anne Marie Grunberg
*Assistant Examiner*—June Hwu
(74) *Attorney, Agent, or Firm*—Klarquist Sparkman LLP

(57) ABSTRACT

Floribunda rose plant having vigorous, rounded plant habit; large flower size; dark green, glossy foliage; sweet, moderate fragrance; and novel orange-pink flower color.

1 Drawing Sheet

Genus and species: *Rosa hybrida.*
Variety denomination: 'JACtosam'.

SUMMARY OF THE INVENTION

The present invention relates to a new and distinct variety of floribunda rose plant named 'JACtosam' which was originated by me by crossing the variety 'JACient.' U.S. Plant Pat. No. 6,725, with an unnamed seedling.

BACKGROUND OF THE INVENTION

The primary objective of this breeding was to produce a new rose variety having the vigorous, rounded plant habit and large flower size of the female parent coupled with the orange flower color and fragance of the male parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Vigorous, rounded plant habit;
2. Large flower size;
3. Dark green, glossy foliage;
4. Sweet, moderate fragrance; and
5. Novel orange-pink flower color.

Asexual reproduction of this new variety by budding, as performed at Wasco, Calif. shows that the foregoing and all other characteristics and distinctions come true to form and are established and transmitted through succeeding propagations.

COMPARISON WITH PARENTS

The subject variety differs from the female parent in flower color in that the female parent is more coral pink versus 'JACtosum's' orange pink and 'JACtosum's ' fragrance is moderate and sweet while the female parent has no fragrance. The male parent possesses orange flowers and the plant habit of the male parent is also more upright.

COMPARISON WITH SIMILAR VARIETY

'JACtosam' differs from 'JACsur' (Bill Warriner)(U.S. Plant Pat. No. 9,494) in that 'JACtosam' has more flower fragrance and longer stems and 'JACsur' has light orange flowers whereas the flowers of 'JACtosam' are yellow-orange in the center of the flower but shade to pink at the outer edge.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (2001), except where ordinary dictionary significance of color is indicated.

Parentage:
*Seed parent.*—'JACient' (U.S. Plant Pat No. 6,725).
*Pollen parent.*—Unnamed seedling. (Unpatented).

FLOWER

Observations made from plants of beginning at two years of age grown in a garden environment at Somis, Calif., January–June, 2002.

Blooming habit: Continuous.
Bud:
*Size.*—About 3 cm long and 2¼ cm in diameter when the petals start to unfurl.
*Form.*—The bud form is pointed ovoid.
*Color.*—When sepals first divide, bud color is Red Group 42A. When half blown, the upper sides of the petals are primarily Orange-Red Group 30D but with Red Group 48D on outer third and Yellow Group 9A at base; and the lower sides of the petals are primarily Orange-Red Group 32A with venation of Yellow Group 9C with Red Group 47C on outer half and a Yellow Group 2B spot at base.

*Sepal.*—Color: Upper surface: Yellow-Green Group 144C in the center with Yellow-Green Group 146C along the side portions. Lower surface: Greyed-Red Group 178A with Green Group 143C along sides. Length: 34–40 mm. Width: 10–12 mm. Shape: Subulate. Surface texture: Upper surface: Hoary. Lower Surface: Smooth. There are three lightly appendaged sepals. There are two unappendaged sepals with ciliate edges.

*Receptacle.*—Color: Green Group 143C. Shape: Funnel. Size: Medium, about 8 mm long×16 mm wide. Surface: Smooth.

*Peduncle.*—Length: Medium, averaging about 5–8 cm. Surface: Glandular. Color: Grey-Brown Group N199A. Strength: Stiff, erect.

Bloom:

*Size.*—Medium. Average open diameter is about 9 cm.

*Borne.*—In flat clusters of 3–5 blooms.

*Stems.*—Strength: Normal. Average length is about 35–45 cm. Diameter: 4–6 mm.

*Form.*—When first open: High centered. Permanence: All petals curl.

*Petalage.*—Number of petals under normal conditions: 25–30.

*Color.*—The upper sides of the petals are Orange Group N25B becoming increasingly Red Group 55C towad tip. The reverse sides of the petals are Red Group 42D becoming increasingly Red Group 55B toward tip. The base of each petal has Yellow Group 9B color spot. The major color on the upper side is Orange Group N25B.

*Variegations.*—Venation of Yellow Group 9C.

*Discoloration.*—The general tonality at the end of the first day: No change. At the end of the third day: Color tends toward Red Group 55B.

*Fragrance.*—Moderate, sweet.

Petals:

*Texture.*—Thick.

*Shape.*—Orbiculate.

*Size.*—Width: 4 cm. Length: 4 cm.

*Surface.*—Smooth.

*Margin.*—Entire. Apex Shape: Obtuse. Base Shape: Between rounded and cuneate.

*Form.*—Tips slightly recurved.

*Arrangement.*—Imbricated.

*Petaloids.*—Number: 1–3. Color: Orange Group N25B on both surfaces. Size: Width: 1–3 mm. Length: 3–8 mm.

*Persistence.*—Petals drop off cleanly before drying.

*Lastingness.*—On the plant: Long (about 5–7 days). As a cut flower: Long (about 7–9 days).

Reproductive parts:

*Stamens.*—Number: 70–80. Length: 12 mm. Anthers: Length: 3 mm. Color: Yellow-Orange Group 18A. Arrangement: Regular Around styles. Filaments: Color: Yellow-Orange Group 18A with Red group 45D over much of the surface. Length: 8–9 mm. Pollen: Color: Yellow-Orange Group 22A.

*Pistils.*—Number: 100–120. Length: 4–5 mm. Styles: Color: Red Group 46B. Length: 3–4 mm. Stigmas: Color: Greyed-Orange Group 168D. Length: 1 mm.

*Hips.*—None observed.

PLANT

*Form.*—Bush.

*Growth.*—Very vigorous, upright and branching.

*Mature plant.*—Height: 100–110 cm at two years of age. Width: 80 cm.

*Rootstock.*—Dr. Huey.

Foliage: Number of leaflets on normal mid-stem leaves: 5.

*Size.*—Medium (150 mm long×130 mm wide).

*Quantity.*—Abundant.

*Color.*—New foliage: Upper side: Greyed-Purple Group 183A. Lower side: Greyed-Purple Group 183A. Old foliage: Upper side: Green Group 139A. Lower side: Green Group N138A.

Leaflets:

*Size.*—About 65 mm long×40 mm wide.

*Shape.*—Ovate.

*Base shape.*—Rounded.

*Apex shape.*—Acuminate.

*Texture.*—Lustrous.

*Edge.*—Serrated.

*Serrations.*—Single, small.

*Petiole.*—Color: Lower surface: Yellow-Green Group 147C; Upper surface: Yellow-Green Group 147A often with Greyed-Purple Group 183C blush.

*Petiole rachis.*—Color: Lower surface: Yellow-Green Group 147C; Upper surface: Yellow-Green Group 147C. Underside: Rough with prickles.

*Stipules.*—Length: 15–18 cm, serrated and with glands. Shape: Adnate and parallel. Upper Surface: Color: Green Group 139. Lower Surface: Color: Green Group N 138A.

*Disease resistance.*—Resistant to mildew and rust and susceptible to blackspot under normal growing conditions.

*Pest resistance.*—Not observed.

*Vein color.*—Same as leaf color.

*Venation pattern.*—Reticulate.

Wood:

*New wood.*—Color: Greyed-Purple Group 183A. Bark: Smooth.

*Old wood.*—Color: Green Group 137C. Bark: Smooth.

Prickles:

*Quantity.*—On main canes from base: Ordinary (15–18 per 150 mm of stem). On laterals from main canes: Ordinary (6–8 per 150 mm of stem).

*Form.*—Curved and hooked upward.

*Length.*—7–11 mm. Average: 9 mm.

*Color when young.*—Greyed-Purple Group 183A.

*Color when mature.*—Greyed-Orange Group 173C.

Small prickles:

*Quantity.*—On main stalks: Few. On laterals: Few.

*Color.*—Young: Greyed-Purple Group 183A. Mature: Greyed-Orange Group 173C.

Winter hardiness: Hardy to Zone 5.

I claim:

1. A new and distinct variety of rose plant of the floribunda class, substantially as herein shown and described, characterized particularly by its vigorous, rounded plant habit; large flower size; dark green, glossy foliage; sweet, moderate fragrance; and novel orange-pink flower color.

* * * * *

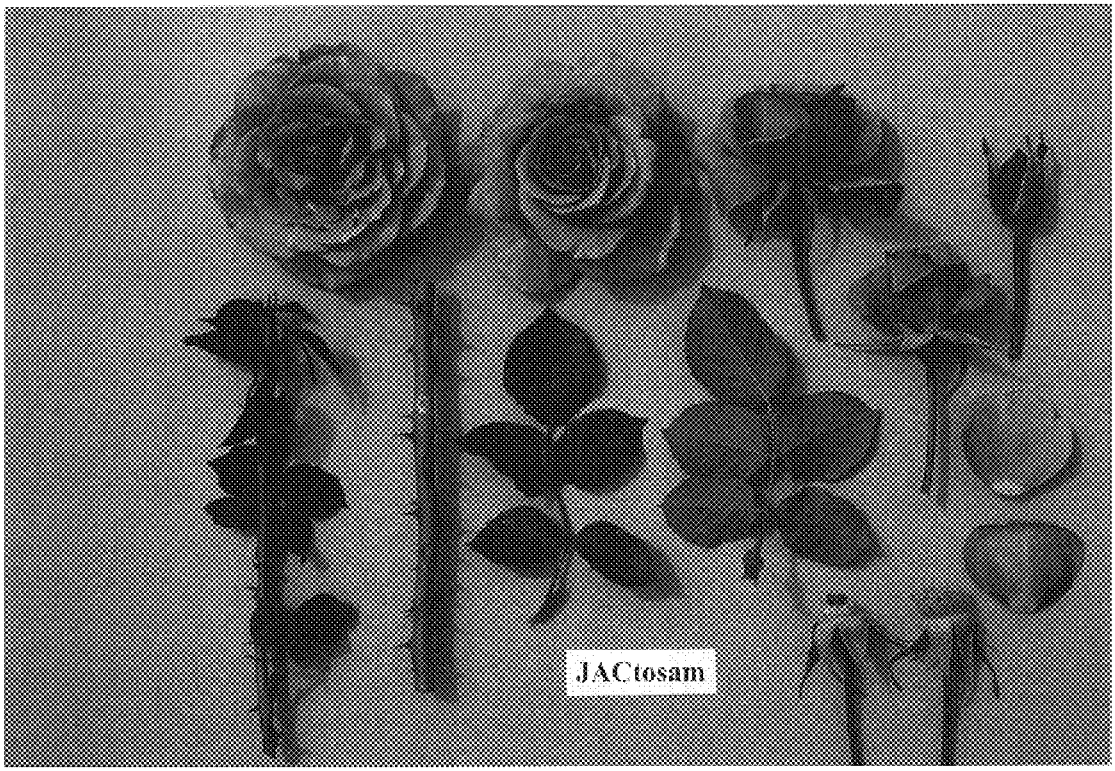
JACtosam